US008257917B2

(12) United States Patent
Wong et al.

(10) Patent No.: US 8,257,917 B2
(45) Date of Patent: Sep. 4, 2012

(54) SALIVARY BIOMARKERS FOR SJÖGREN'S SYNDROME

(75) Inventors: David T. W. Wong, Beverly Hills, CA (US); Shen Hu, Simi Valley, CA (US); Jianghua Wang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 345 days.

(21) Appl. No.: 12/475,347

(22) Filed: May 29, 2009

(65) Prior Publication Data

US 2010/0021906 A1 Jan. 28, 2010

Related U.S. Application Data

(60) Provisional application No. 61/087,491, filed on Aug. 8, 2008, provisional application No. 61/056,959, filed on May 29, 2008.

(51) Int. Cl.
*C12Q 1/70* (2006.01)
*C12Q 1/68* (2006.01)

(52) U.S. Cl. ............... 435/5; 435/6.1; 435/7.1; 435/7.2

(58) Field of Classification Search ............... 435/5, 6.1, 435/7.1, 7.2
See application file for complete search history.

(56) References Cited

U.S. PATENT DOCUMENTS

2006/0269968 A1 11/2006 Fasano
2007/0148676 A1 6/2007 Kachalsky et al.

OTHER PUBLICATIONS

Baechler, E.C. et al., "Gene expression profiling in human autoimmunity," *Immunological Reviews*, 2006, vol. 210, pp. 120-137.
Båve, U. et al., "Activation of the Type I Interferon System in Primary Sjögren's Syndrome," *Arthritis & Rheumatism*, Apr. 2005, vol. 52, No. 4, pp. 1185-1195.
Ben-Chetrit, E. et al., "Anti-SSA/Ro and Anti-SSB/La Antibodies in Serum and Saliva of Patients with Sjogren's Syndrome," *Clinical Rheumatology*, 1993, vol. 12, No. 4, pp. 471-474.
Castro, J. et al., "Salivary and serum β2-microglobulin and gamma-glutamyl-transferase in patients with primary Sjögren syndrome and Sjögren syndrome secondary to systemic lupus erythematosus," *Clinica Chimica Acta*, 2003, vol. 334, pp. 225-231.
Der, S.D. et al., "Identification of genes differentially regulated by interferon α, β, or γ using oligonucleotide arrays," *Proc. Natl. Acad. Sci. USA*, Dec. 1998, vol. 95, pp. 15623-15628.
Espinosa, A. et al., "The Sjögren's Syndrome-Associated Autoantigen Ro52 Is an E3 Ligase That Regulates Proliferation and Cell Death," *The Journal of Immunology*, 2006, vol. 176, pp. 6277-6285.
Ferraccioli, G.F. et al., "Interferon alpha-2 (IFNα2) increases lacrimal and salivary function in Sjögren's syndrome patients. Preliminary results of an open pilot trial versus OH-chloroquine," *Clinical and Experimental Rheumatology*, 1996, vol. 14, pp. 367-371.

(Continued)

*Primary Examiner* — Jezia Riley
(74) *Attorney, Agent, or Firm* — Morgan, Lewis & Bockius LLP; Annette S. Parent

(57) ABSTRACT

The present invention provides for the first time the identification of salivary protein and RNA factors that can be used in the detection of primary Sjögren's Syndrome. The present invention therefore provides methods of diagnosing and providing a prognosis for Sjögren's Syndrome, by examining relevant proteins (including certain autoantigens and autoantibodies) and RNA in a patient's saliva.

12 Claims, 5 Drawing Sheets

OTHER PUBLICATIONS

Gottenberg, J-E. et al., "Activation of IFN pathways and plasmacytoid dendritic cell recruitment in target organs of primary Sjögren's syndrome," *PNAS*, Feb. 21, 2006, vol. 103, No. 8, pp. 2770-2775.

Hjelmervik, T.O.R. et al., "Gene Expression Profiling of Minor Salivary Glands Clearly Distinguishes Primary Sjögren's Syndrome Patients From Healthy Control Subjects," *Arthritis & Rheumatism*, May 2005, vol. 52, No. 5, pp. 1534-1544.

Hu, S. et al., "Differentially expressed protein markers in human submandibular and sublingual secretions," *International Journal of Oncology*, 2004, vol. 25, pp. 1423-1430.

Hu, S. et al., "Large-scale identification of proteins in human salivary proteome by liquid chromatography/mass spectrometry and two-dimensional gel electrophoresis-mass spectrometry," *Proteomics*, 2005, vol. 5, pp. 1714-1728.

Hu, S. et al., "Human Saliva Proteome and Transcriptome," *Journal of Dental Research*, 2006, vol. 85, No. 12, pp. 1129-1133.

Hu, S. et al., "Discovery of Oral Fluid Biomarkers for Human Oral Cancer by Mass Spectrometry," *Cancer Genomics Proteomics*, 2007, vol. 4, pp. 56-64.

Hu, S. et al., "Salivary Proteomic and Genomic Biomarkers for Primary Sjögren's Syndrome," *Arthritis & Rheumatism*, Nov. 2007, vol. 56, No. 11, pp. 3588-3600.

International Search Report mailed on Sep. 9, 2009, for International Application No. PCT/US09/45718, filed on May 29, 2009, 2 pages.

Li, Y. et al., "RNA Profiling of Cell-free Saliva Using Microarray Technology," *Journal of Dental Research*, 2004, vol. 83, No. 3, pp. 199-203.

Li, Y. et al., "Salivary Transcriptome Diagnostics for Oral Cancer Detection," *Clinical Cancer Research*, Dec. 15, 2004, vol. 10, pp. 8442-8450.

Maddali Bongi, S. et al., "The Diagnosis Value of β2-Microglobulin and Immunoglobulins in Primary Sjögren's Syndrome," *Clinical Rheumatology*, 1995, vol. 14, No. 2, pp. 151-156.

McArthur, C.P. et al., "Monoclonal Antibody Detection of Laminin in Minor Salivary Glands of Patients with Sjögren's Syndrome," *Journal of Autoimmunity*, 1993, vol. 6, pp. 649-661.

Navazesh, M., "Methods for Collecting Saliva," *Annals of New York Academy of Sciences*, 1993, vol. 694, pp. 72-77.

Nordmark, G. et al., "Mechanisms of Disease: primary Sjögren's syndrome and the type I interferon system," *Nature Clinical Practice Rheumatology*, May 2006, vol. 2, No. 5, pp. 262-269.

O'Dwyer, D.T. et al., "Identification of the 49-kDa Autoantigen Associated with Lymphocytic Hypophysitis as α-Enolase," *The Journal of Clinical Endocrinology & Metabolism*, 2002, vol. 87, No. 2, pp. 752-757.

Ochi, H. et al., "Proteomic analysis of human brain identifies α-enolase as a novel autoantigen in Hashimoto's encephalopathy," *FEBS Letters*, 2002, vol. 528, pp. 197-202.

Pijpe, J. et al., "Progression of salivary gland dysfunction in patients with Sjögren's syndrome," *Ann. Rheum. Dis.*, 2006, vol. 66, pp. 107-112.

Pijpe, J. et al., "Parotid gland biopsy compared with labial biopsy in the diagnosis of patients with primary Sjögren's syndrome," *Rheumatology*, 2007, vol. 46, pp. 335-341.

Pratesi, F. et al., "Autoantibodies Specific for α-Enolase in Systemic Autoimmune Disorders," *The Journal of Rheumatology*, 2000, vol. 27, No. 1, pp. 109-115.

Ramachandran, P., "Identification of N-Linked Glycoproteins in Human Saliva by Glycoprotein Capture and Mass Spectrometry," *Journal of Proteome Research*, 2006, vol. 5, No. 6, pp. 1493-1503.

Ryu, O.H. et al., "Identification of parotid salivary biomarkers in Sjögren's syndrome by surface-enhanced laser desorption/ionization time-of-flight mass spectrometry and two-dimensional difference gel electrophoresis," *Rheumatology*, 2006, vol. 45, pp. 1077-1086.

Sanda, C. et al., "Differential Gene Induction by Type 1 and Type II Interferons and Their Combination," *Journal of Interferon & Cytokine Research*, 2006, vol. 26, pp. 462-472.

Sfriso, P. et al., "Serum and salivary neopterin and interferon-γ in primary Sjögren's syndrome," *Scand. J. Rheumatol.*, 2003, vol. 32, pp. 74-78.

Shiozawa, S. et al., "Single-Blinded Controlled Trial of Low-Dose Oral IFN-α for the Treatment of Xerostomia in Patients with Sjögren's Syndrome," *Journal of Interferon & Cytokine Research*, 1998, vol. 18, pp. 255-262.

Swaak, A.J.G. et al., "Diagnostic significance of salivary levels of β2-microglobulin in Sjögren's syndrome," *Clinical Rheumatology*, 1988, vol. 7, No. 1, pp. 28-34.

Tishler, M. et al., "Salivary and serum soluble interleukin-2 receptor in primary Sjögren's syndrome," *Archives of Oral. Biology*, 1999, vol. 44, pp. 305-308.

Tomosugi, N. et al., "Diagnostic Potential of Tear Proteomic Patterns in Sjögren's Syndrome," Journal of Proteome Research, 2005, vol. 4, No. 3, pp. 820-825.

Vitali, S. et al., "Classification criteria for Sjögren's syndrome: a revised version of the European criteria proposed by the American-European Consensus Group," *Ann. Rheum. Dis.*, 2002, vol. 61, pp. 554-558.

Wang, J. et al., "Salivary RNA Biomarker Candidates for Primary Sjögren's Syndrome," presentation poster at the Meeting of Oral-Based Diagnosis, Oct. 10-13, 2006, Georgia, Atlanta.

Witte, T., "Antifodrin Antibodies in Sjögren's Syndrome, A Review," *Ann. N.Y. Acad. Sci.*, 2005, vol. 1051, pp. 235-239.

SALIVARY BIOMARKERS FOR SJÖGREN'S SYNDROME

CROSS-REFERENCES TO RELATED APPLICATIONS

This application is related to U.S. Provisional Application No. 61/056,959 filed on May 29, 2008, entitled "Salivary Biomarkers for Sjögren's Syndrome," and U.S. Provisional Application No. 61/087,491, filed on Aug. 8, 2008, also entitled "Salivary Biomarkers for Sjögren's Syndrome," the disclosures of which are incorporated by reference herein in their entirety for all purposes.

STATEMENT AS TO RIGHTS TO INVENTIONS MADE UNDER FEDERALLY SPONSORED RESEARCH OR DEVELOPMENT

This invention was made with Government support under Grant No. RO1-DE17593 awarded by the NIH. The Government has certain rights in this invention.

BACKGROUND OF THE INVENTION

Sjögren's syndrome is an autoimmune disorder in which immune cells attack and destroy the exocrine glands that produce tears and saliva. It is named after Swedish ophthalmologist Henrik Sjögren (1899-1986), who first described it. Sjögren's syndrome is also associated with rheumatic disorders such as rheumatoid arthritis, and it is rheumatoid factor positive in 90 percent of cases. The hallmark symptoms of this disorder are dry mouth and dry eyes (part of what are known as sicca symptoms). In addition, Sjögren's syndrome may cause skin, nose, and vaginal dryness, and may affect other organs of the body, including the kidneys, blood vessels, lungs, liver, pancreas, and brain. Nine out of ten Sjögren's patients are women and the average age of onset is late 40 s, although Sjögren's occurs in all age groups in both women and men. It is estimated to strike as many as 4 million people in the United States alone making it the second most common autoimmune rheumatic disease. Thus, there exists a clear need for better, more effective diagnostic and therapeutic methods for this condition. The present invention meets this and other related needs by identifying biomarkers, such as proteins and nucleic acids, present in human saliva that can be used for diagnosing Sjögren's syndrome.

BRIEF SUMMARY OF THE INVENTION

In one aspect, the present invention provides a method for diagnosing Sjögren's Syndrome in a subject. The method comprises the steps of: (a) analyzing a saliva sample from the subject with an assay that specifically detects the level of a marker selected from Table 1, Table 3, Table 4, or FIG. 4; and (b) determining whether the marker level is increased or decreased from a standard control by comparing the marker level with the control; thereby providing a diagnosis for Sjögren's Syndrome.

In another aspect, the present invention provides a method of providing a prognosis for Sjögren's Syndrome. The method includes the steps of: (a) analyzing a saliva sample from the subject with an assay that specifically detects the level of a marker selected from Table 1, Table 3, Table 4, or FIG. 4; and (b) determining whether the marker level is increased or decreased from a standard control by comparing the marker level with the control; thereby providing a prognosis for Sjögren's Syndrome.

In yet another aspect, the present invention provides a method of monitoring the efficacy of a treatment for Sjögren's Syndrome. The method includes the steps of: (a) analyzing a saliva sample from the subject with an assay that specifically detects the level of a marker selected from Table 1, Table 3, Table 4, or FIG. 4; and (b) determining whether the marker level is increased or decreased from a standard control by comparing the marker level with the control; thereby monitoring the efficacy of the treatment for Sjögren's Syndrome.

In one embodiment, the assay detects protein and is ELISA, Western blotting, flow cytometry, immunofluorescence, immunohistochemistry, or mass spectroscopy. In another embodiment, the assay detects nucleic acid and is mass spectroscopy, PCR, microarray hybridization, thermal cycle sequencing, capillary array sequencing, or solid phase sequencing.

In one embodiment, the assay comprises a reagent that binds to a protein. For example, the reagent may be an antibody, especially a monoclonal antibody. In other embodiment, the assay comprises a reagent that binds to a nucleic acid. For example, the reagent itself may be a nucleic acid, such as an oligonucleotide, especially one serving as an RT-PCR primer.

In one embodiment, the marker is one or more proteins selected from proteins 1-16 of Table 1 and a decreased marker level indicates Sjögren's Syndrome. In another embodiment, the marker is one or more proteins selected from proteins 18-42 of Table 1 and an increased marker level indicates Sjögren's Syndrome. In another embodiment, the marker is one or more proteins selected from Table 3 and an increased marker level indicates Sjögren's Syndrome. In another embodiment, the marker is one or more mRNA selected from Table 4 and an increased marker level indicates Sjögren's Syndrome. In yet another embodiment, the marker is one or more mRNA selected from FIG. 4, and particularly from Table 2, and an increased marker level indicates Sjögren's Syndrome.

BRIEF DESCRIPTION OF THE DRAWINGS

FIG. 1B presents the 2-D gel patterns of proteins in pooled WS from 10 pSS or 10 matched control subjects. 100 μg of total proteins from each pooled sample was used for 2-D gel separation. The differentially expressed proteins (spots number 1-42) were identified using in-gel tryptic digestion and LC-QqTOF MS.

DETAILED DESCRIPTION OF THE INVENTION

Introduction

Figure 1:
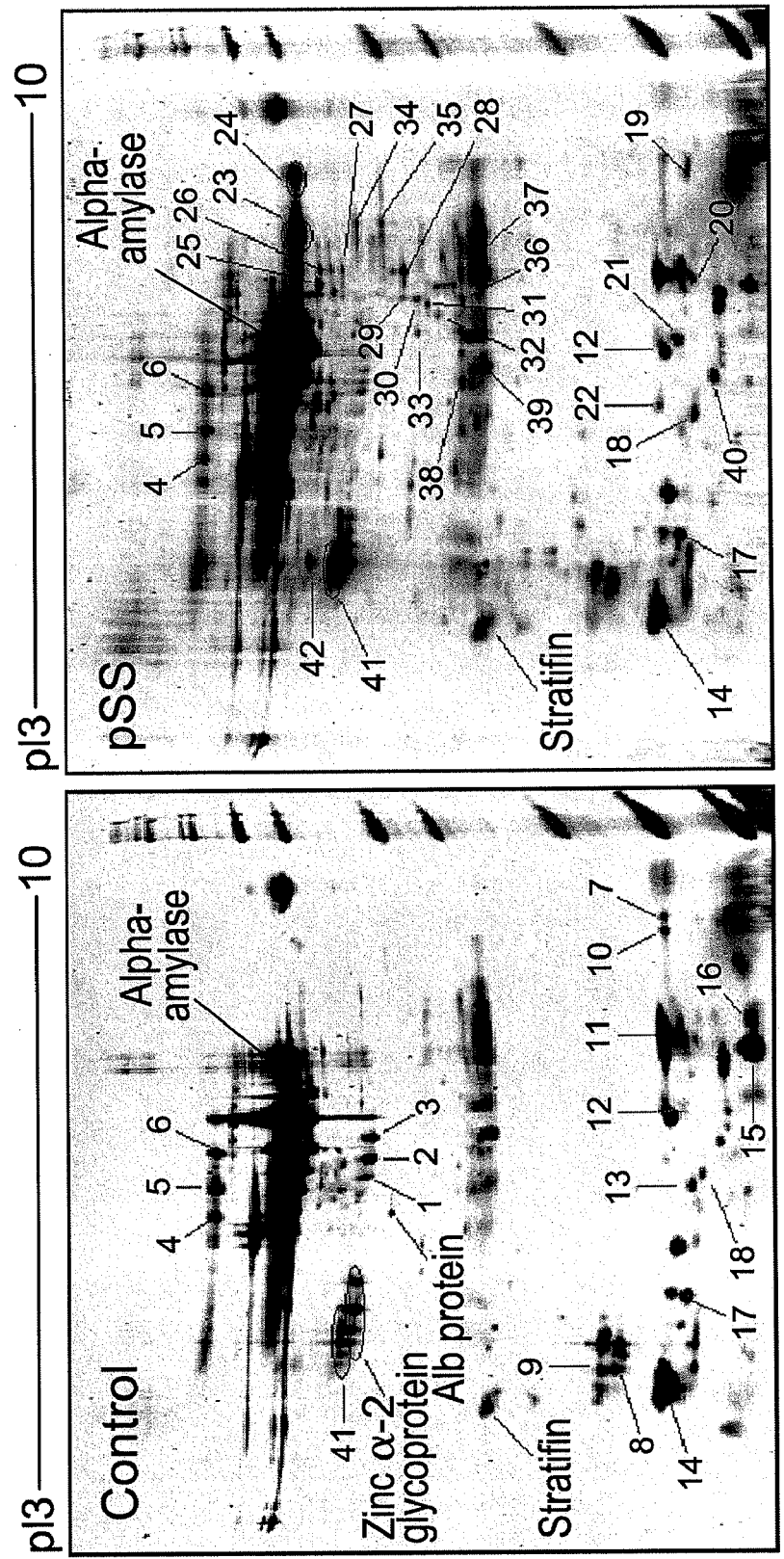
FIG. 1: Comparative analysis of saliva peptides and proteins between pSS and matched control subjects using MALDI-TOF MS and 2-DGE/LC-QqTOF MS. MALDI-MS profiling of peptides in WS from a pSS and a matched control subject is shown in FIG. 1A. α-Cyano-4-hydroxycinnamic acid (10 mg/ml) was used as the matrix for MALDI-MS measurement.

Sjögren's syndrome (SS), first described by the Swedish physician Henrik Sjögren in 1933 (Sjogren, H., *Acta Opthalmol* 1933; 11(suppl 2):1-151), is a chronic autoimmune disorder clinically characterized by a dry mouth (xerostomia) and dry eyes (keratoconjunctivitis sicca). The disease primarily affects women, at a ratio of 9:1 over men. While SS affects up to 4 million Americans, about half are primary Sjögren's Syndrome (pSS). pSS occurs alone while secondary Sjögren's Syndrome (sSS) presents in connection with other autoimmune diseases such as rheumatoid arthritis (RA) or systemic lupus erythematosus (SLE). Histologically SS is characterized by infiltration of exocrine glandular tissue by predominantly CD4 T lymphocytes. At the molecular level the glandular epithelial cells express high levels of HLA-DR, leading to the speculation that these cells are presenting antigen (viral or autoantigen) to the invading T cells. Cytokine production follows, with IFN and IL-2 being especially important. There is also evidence of B cell activation with autoantibody production and an increase in B cell malignancy. SS patients exhibit a 40-fold increased risk for lymphoma.

SS is a complex disease that can go undiagnosed for several months to years. Although the underlying immuno-mediated glandular destruction is thought to develop slowly over several years, a long delay from the start of the symptoms to final diagnosis has been frequently reported. SS presumably involves interplay of genetic and environmental factors. To date few of these factors are well understood. As a result, there is a lack of early diagnostic markers and diagnosis usually lags onset by years. A new international consensus for diagnosis requires objective signs and symptoms of dryness including a characteristic appearance of a biopsy sample from a minor or major salivary gland and/or autoantibody such as anti-SS-A (Vitali et al., *Ann Rheum Dis* 2002; 61(6):554-8; Fox, R., *Lancet* 2005; 366(9482):321-31; Pijpe et al., Parotid gland biopsy compared with labial biopsy in the diagnosis of patients with primary Sjögren's syndrome, *Rheumatology* (Oxford) 2006; Epub ahead of print). However, establishing the diagnosis of SS has been difficult in light of its nonspecific symptoms (dry eyes and mouth) and lack of both sensitive and specific biomarkers, either body fluid or tissue-based, for pSS detection. It is widely believed that developing molecular biomarkers for early pSS diagnosis will improve the application of systematic therapies and setting of criteria to monitor therapies and assess prognosis (e.g., lymphoma development).

Saliva is the product of three pairs of major salivary glands, parotid (PAR), submandibular (SM) and sublingual (SL), and multiple minor salivary glands lying beneath the oral mucosa. Human saliva contains many informative proteins that can be used for detection of human diseases. Saliva is an attractive diagnostic fluid because salivary testing provides several key advantages including low cost, non-invasiveness, and easy sample collection and processing. Human saliva collection is less invasive than that of blood for serum/plasma analyses and many if not all blood components are indeed reflected in saliva. This bio-fluid has been used for survey of the general health and diagnosis of human diseases such as HIV, periodontal diseases and autoimmune diseases (Malamud, D., *Am J Med* 1997; 102(4A):9-14; Kaufman, E. and Lamster, I B., *J Clin Periodontol* 2000; 27:453-65; Kalk et al., *Ann Rheum Dis* 2002; 61(2):137-44; Pijpe et al., Progression of salivary gland dysfunction in patients with Sjogren's syndrome, *Ann Rheum Dis* 2006; Epub ahead of print). The salivary glands are one of the major exocrine glands affected in pSS patients. Within the spectrum of clinical manifestations of SS, salivary gland dysfunction is considered one of the key manifestations. As much as salivary glandular biopsy will reveal the pathognomonic predominant CD4 T lymphocytic infiltration into the salivary glandular parenchyma, it is logical to envision that pathognomonic and signature biomarkers are shed by the affected salivary parenchymal cells and the infiltrated lymphocytes into saliva that drains the affected gland. The research group led by the present inventors is active towards the comprehensive analysis of the saliva proteome (www.hspp.ucla.edu), providing the technologies and expertise to contrast proteomic constituents in pSS with that in control saliva (Hu et al., *Proteomics* 2005; 5(6):1714-28; Hu et al., *Int J Oncol* 2004; 25(5):1423-30; Ramachandran, P., *J Proteome Res* 2006; 5(6):1493-503). Thus far the inventors have identified over 1000 proteins in whole saliva (WS). In addition, the inventors have recently identified and catalogued ~3000 mRNAs in human WS (Li et al., *J Dent Res* 2004; 83(3):199-203). These studies have provided a solid foundation for saliva biomarker discovery in pSS patients. The inventors' group has previously demonstrated proteome- and genome-wide approaches to harness saliva protein and mRNA signatures for human oral cancer detection (Hu et al., Discovery of oral fluid biomarkers for human oral cancer using mass spectrometry, Cancer Genomics Proteomics 2006; in press; Li et al., Clin Cancer Res 2004; 10(24):8442-50).

There have been continuous efforts on searching for biomarkers in human serum or saliva for diagnosis of pSS. Some gene products were found at elevated levels in SS patients' serum or saliva, including beta-2-microglobulin (B2M), soluble interleukin-2 receptor, interleukin-6, anti-Ro/SS-A, anti-La/SS-B and anti-alpha-fodrin autoantibodies (Castro et al., *Clin Chim Acta* 2003; 334(1-2):225-31; Tishler et al., *Arch Oral Biol* 1999; 44(4):305-8; Tishler et al., *Rheumatol Int* 1999; 18(4):125-7; Sfriso et al., *Scand J Rheumatol* 2003; 32(2):74-8; Ben-Chetrit et al., *Clin Rheumatol* 1993; 12(4):471-4; Witte, T., *Ann NY Acad Sci* 1995; 1051:235-9). However, none of them are individually sensitive or specific enough for confirmative diagnosis of SS (Castro et al., *Clin Chim Acta* 2003; 334(1-2):225-31). Therefore, it is crucial to utilize emerging proteome- and genome-wide approaches to discover a wide spectrum of informative and discriminatory biomarkers that can be combined to improve the sensitivity and specificity for pSS detection.

Definitions

As used in this application, an "increase" or a "decrease" refers to a detectable positive or negative change in quantity from an established standard control. An increase is a positive change preferably at least 10%, more preferably 50%, still more preferably 2-fold, even more preferably at least 5-fold, and most preferably at least 10-fold of the control value. Similarly, a decrease is a negative change preferably at least 10%, more preferably 50%, still more preferably at least 80%, and most preferably at least 90% of the control. Other terms indicating quantitative changes or differences from a comparative basis, such as "more" or "less," are used in this application in the same fashion as described above.

Figure 4:
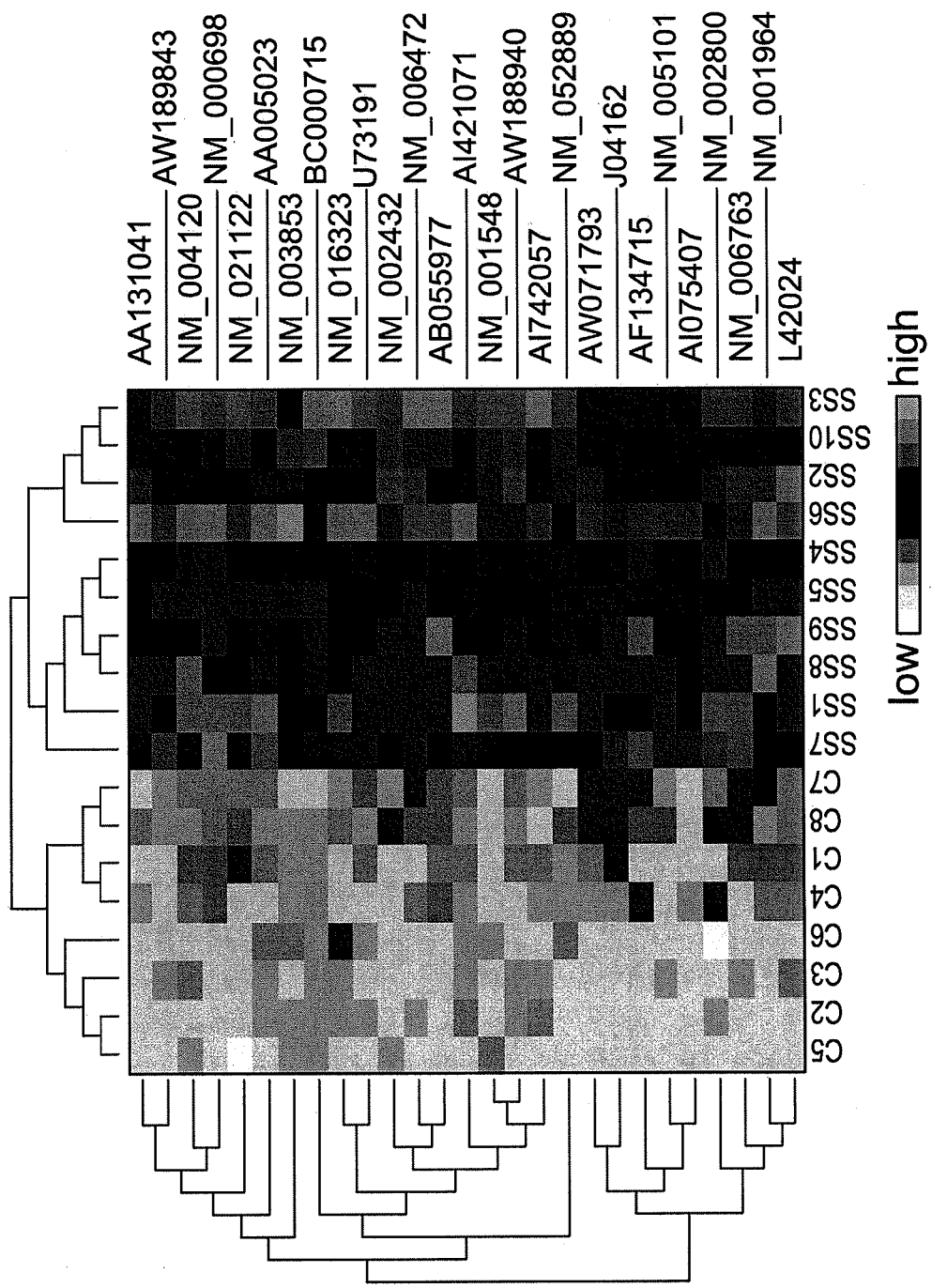
FIG. 4: The heatmap of 27 significantly up-regulated mRNAs between pSS and matched control subjects as obtained by microarray profiling analysis.

"Primers" as used herein refer to oligonucleotides that can be used in an amplification method, such as a polymerase chain reaction (PCR), to amplify a nucleotide sequence based on the polynucleotide sequence corresponding to a sequence of interest, e.g., any mRNA in FIG. 4, based on the Watson-Crick base-pair complementarity principle.

"Standard control value" as used herein refers to a predetermined amount of a particular protein or nucleic acid that is detectable in a saliva sample, either in whole saliva or in saliva supernatant. The standard control value is suitable for the use of a method of the present invention, in order for comparing the amount of a protein or nucleic acid of interest that is present in a saliva sample. An established sample serving as a standard control provides an average amount of the protein or nucleic acid of interest in the saliva that is typical for an average, healthy person of reasonably matched background, e.g., gender, age, ethnicity, and medical history. A standard control value may vary depending on the protein or nucleic acid of interest and the nature of the sample (e.g., whole saliva or supernatant).

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3)

Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:

323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

Diagnostic and Prognostic Methods

The present invention provides methods of diagnosing autoimmune disease Sjögren's Syndrome by examining relevant proteins (such as those listed in Table 1), autoantigens and their autoantibodies (such as those listed in Table 3), or mRNA species (such as those provided in Table 4, FIG. 4 and subset of which in Table 2), or a combination thereof in saliva samples, including wild-type, truncated or alternatively spliced forms of these proteins/autoantigens. Diagnosis involves determining the level of a polypeptide or polynucleotide of the invention in a patient and then comparing the level to a baseline or range. Typically, the baseline value is representative of a polypeptide or polynucleotide of the invention in a healthy person not suffering from Sjögren's Syndrome, as measured using saliva samples processed in the same manner. Variation of levels of a polypeptide or polynucleotide of the invention from the baseline range (either up or down) indicates that the patient has Sjögren's Syndrome or is at risk of developing Sjögren's Syndrome.

As used herein, the term "providing a prognosis" refers to providing a prediction of the probable course and outcome of Sjögren's Syndrome, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

Antibody reagents can be used in assays to detect expression levels of the relevant proteins and/or autoantigens in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., *Curr. Opin. Biotechnol.*, 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., *Electrophoresis*, 18:2184-93 (1997); Bao, *J. Chromatogr. B. Biomed. Sci.*, 699:463-80 (1997). Liposome immunoassays, such as flow-injection liposome immunoassays and liposome immunosensors, are also suitable for use in the present invention. See, e.g., Rongen et al., *J. Immunol. Methods*, 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.*, 27:261-276 (1989)).

Specific immunological binding of the antibody to relevant nucleic acids (such as the mRNA species named in FIG. 3) can be detected directly or indirectly. Direct labels include fluorescent or luminescent tags, metals, dyes, radionuclides, and the like, attached to the antibody. An antibody labeled with iodine-125 ($^{125}I$) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), in the physical form of sticks, sponges, papers, wells, and the like. An assay strip can be prepared by coating the antibody or a plurality of antibodies in an array on a solid support. This strip can then be dipped into the test sample and processed quickly through washes and detection steps to generate a measurable signal, such as a colored spot.

Alternatively, nucleic acid binding molecules such as probes, oligonucleotides, oligonucleotide arrays, and primers can be used in assays to detect differential mRNA expression in patient samples, e.g., RT-PCR. In one embodiment, RT-PCR is used according to standard methods known in the art. In another embodiment, PCR assays such as Taqman® assays available from, e.g., Applied Biosystems, can be used to detect nucleic acids and variants thereof. In other embodiments, qPCR and nucleic acid microarrays can be used to detect nucleic acids. Reagents that bind to selected cancer biomarkers can be prepared according to methods known to those of skill in the art or purchased commercially.

Analysis of nucleic acids can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Chee et al., *Science*, 274:610-614 (1996); Drmanac et al., *Science*, 260:1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.*, 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection. Other useful physical formats include sticks, wells, sponges, and the like.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to patient samples immobilized on microscope slides. The resulting antibody staining or in situ hybridization pattern can be visualized using any one of a variety of light or fluorescent microscopic methods known in the art.

Analysis of the protein or nucleic acid can also be achieved, for example, by high pressure liquid chromatography (HPLC), alone or in combination with mass spectrometry (e.g., MALDI/MS, MALDI-TOF/MS, tandem MS, etc.).

Compositions, Kits and Integrated Systems

The invention provides compositions, kits and integrated systems for practicing the assays described herein using antibodies specific for the polypeptides or nucleic acids specific for the polynucleotides of the invention.

Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize multiple proteins/autoantigens provided in Tables 1 and 3 or oligonucleotide probes that specifically hybridize multiple mRNA sequences provided in Table 4, FIG. 4, or Table 2.

EXAMPLES

The following examples are offered to illustrate, but not to limit the claimed invention.
Objective. To discover a panel of protein and mRNA biomarkers in human whole saliva (WS) for potential detection of primary Sjögren's Syndrome (pSS).
Methods. Mass spectrometry and expression microarray profiling were used to identify candidate protein and mRNA biomarkers in WS for pSS. Validation of discovered mRNA and protein biomarkers was also demonstrated using real-time quantitative PCR (RT-qPCR) and immunoblotting.
Results. Sixteen WS proteins were found down-regulated and 25 WS proteins were found up-regulated in pSS patients compared to matched control subjects. These proteins reflected the damage of glandular cells and inflammation of oral cavity system in pSS patients. In addition, 16 WS peptides (10 up-regulated & 6 down-regulated in pSS) were found at significantly differential levels ($p<0.05$) between pSS and control groups. Under stringent criteria (3-fold change, $p<0.0005$), 27 saliva mRNAs were found significantly up-regulated in the pSS patients. Strikingly, 19 out of 27 over-expressed genes were interferon inducible or related to lymphocyte filtration and antigen presentation known to be involved in pSS pathogenesis.
Conclusion. Our preliminary study has indicated that the WS of patients with pSS contains molecular signatures reflecting the damage of glandular cells and activated immune response for this autoimmune disease. These candidate proteomic and genomic biomarkers may improve the clinical detection of pSS once further validated. We have also revealed that WS contains more informative proteins, peptides and mRNAs than gland specific saliva towards generating candidate biomarkers for pSS detection.
Methods
Patient Cohort Because sample quality is critical for clinical proteomics studies, a standardized procedure, in strict accordance with the US-European Sjögren's Syndrome Classification criteria, has been used towards the identification and recruitment of pSS patients for this study. The diagnostic work-up for SS, carried out in all patients, included: subjective complaints of oral and ocular dryness, sialometry (unstimulated WS), sialography, histopathology of salivary gland tissue, serology (SS-A and SS-B antibodies) and eye tests (Rose Bengal staining and Schirmer test) according to the American-European classification criteria for SS (Vitali et al., *Ann Rheum Dis* 2002; 61(6):554-8), and screening for extra-glandular manifestations. Three pSS patients were treated with Plaquenil and one patient was treated with Prednisolon. Eight patients had focus score>1 through parotid gland biopsy examination. The enrolled pSS and control subjects are well matched in age, gender and ethnicity. The average age was 37.2±9.8 years for the pSS patients (n=10) and 37.0±10.6 years for the control subjects (n=10). All the subjects enrolled for this study are Caucasian women as pSS is primarily a female disease. All the enrolled control subjects were negative for serum anti-SSA/SSB. There were no SICCA complaints including oral and ocular dryness.
Saliva Sample Collection Whole, PAR and SM/SL saliva were collected from each pSS and control subject for comparative analysis. Saliva sample collection was performed at the University Medical Center Groningen, the Netherlands, using our standardized saliva collection protocols. Subjects were asked to refrain from eating, drinking, smoking or oral hygiene procedures for at least one hour prior to the collection. Samples were collected in the morning at least two hours after eating and rinsing mouth with water using established protocols (Burlage et al., *Eur J Oral Sci* 2005; 113(5):386-90; Navazesh, M., *Ann NY Acad Sci* 1993; 694:72-7). WS was paraffin stimulated and collected during 15 minutes. Glandular saliva specimens from both individual PAR glands and, simultaneously, from the SM/SL glands were collected by Lashley cups (placed over the orifices of the Stenson's duct) and syringe aspiration (from the orifices of the Warton's duct located anteriorly in the floor of the mouth), respectively. After collection, saliva samples were immediately mixed with protease inhibitors (Sigma, St. Louis, Mo.) to ensure preservation integrity of proteins and then centrifuged at 2,600 g for 15 min at 4° C. The supernatant was removed from the pellet, immediately aliquoted and stored at −80° C. All the samples were kept on ice during the process. Patient 2 and patient 10 did not produce enough SM/SL saliva for this study because these two patients' SM/SL saliva flow rates were very low at 0.03 ml/min (Table 1).
Sample Preparation for Proteomic Analysis The saliva samples were precipitated by cold ethanol at −20° C. for overnight. Following centrifugation at 14,000 g for 20 min, the supernatants were collected and dried using a speed vacuum for peptide biomarker study. The pellet was then washed once with cold ethanol and collected for total protein assay using 2-D Quant Kit (Amersham, Piscataway, N.J.). Due to limited saliva sample volume from the pSS patients, we equally pooled the saliva samples from all pSS patients or all control subjects, respectively, for the 2-D gel analysis. However, both pSS and control subjects were individually analyzed for the peptide profiling experiment.
Matrix-Assisted Laser Desorption/Ionization Time-of-Flight Mass Spectrometry (MALDI-TOF MS)

Profiling of saliva peptides in 10 pSS and 10 matched control subjects was performed using MALDI-TOF MS (Applied Biosystems, Foster City, Calif.). The peptide fraction from each patient (n=10) and control (n=10) samples was dissolved in 10 µL of 50% ACN/0.1% TFA. Sample was mixed with α-cyano-4-hydroxycinnamic acid (CHCA, 10 mg/mL in 50% ACN/0.1% TFA) in a ratio of 1:2, and 1 µL of the mixture was spotted on the MALDI plate for measurements. Three measurements were performed for each sample and the signals were averaged for subsequent data analysis.

In order to realize accurate comparison of MALDI-MS data between pSS and matched control groups, baseline correction and Gaussian smoothing were initially performed to eliminate broad artifacts and noise spikes. Afterwards, peak alignment was undertaken to ensure accurate alignment of m/z values across the set of spectra, and peak normalization was performed against total peak intensity. These steps ensure comparability of MALDI spectra among all subjects. Subsequent statistical analysis (t-test) was used to reveal peptides at significantly differential levels between pSS and control patients.

2-D Gel Electrophoresis (2-DGE)

The saliva samples were equally pooled from either 10 pSS or 10 control patients according to the total protein amount and then precipitated using the same procedures described above. The pellet was washed once with cold ethanol and then re-suspended in rehydration buffer. In total, 100 µg of proteins were loaded onto each gel for 2-D gel separation. Isoelectric focusing (IEF) was performed using immobilized pH gradient strips (11-cm length, pI 3-10 NL) on a Protean (Bio-Rad) IEF cell, and SDS-PAGE was performed in 8-16% precast Criterion gels on a Criterion Dodeca Cell (Bio-Rad, Hercules, Calif.). Fluorescent Sypro-Ruby stain (Invitrogen, Carlsbad, Calif.) was finally used to visualize protein spots.

The gel images were acquired and analyzed using PDQuest software (Bio-Rad). The images were initially processed through transformation, filtering, automated spot detection, normalization, and matching. The 2-D gel image was transformed to adjust the intensity of the protein spot, and filtered to remove small noise features without affecting the protein spot. Finally, the images were normalized based on the total density in gel image. A matchset was created between the 2-D gel image of the pSS sample (master gel) and the one of control sample using automated detection to detect the protein spots on gel. Within the matchset, the spots detected were reviewed manually, and the relative levels between the disease and control patients were summarized.

Liquid Chromatography-Tandem Mass Spectrometry (LC-MS/MS) and Database Searching Protein spots showing differential protein levels were excised by a spot-excision robot (Proteome Works, Bio-Rad) and deposited into 96-well plates. Proteins in each gel spots were reduced with DTT and alkylated with iodoacetamide and finally digested with 10 ng trypsin at 37° for overnight. After digestion, the peptides were extracted and stored at −80° C. prior to LC-MS/MS analysis.

LC-MS/MS analysis of peptides was performed using a LC Packings nano-LC system (Sunnyvale, Calif., USA) with a nanoelectrospray interface (Protana, Odense, Denmark) and quadrupole time-of-flight (QqTOF) mass spectrometer (Applied Biosystems, QSTAR XL). A New Objective (Woburn, Mass., USA) PicoTip tip (I. D., 8 mm) was used for spraying with the voltage at 1850 V for online MS and MS/MS analyses. The samples were first loaded onto a LC Packings Pep-Map C18 precolumn (300 µm×1 mm; particle size 5 µm) and then injected onto a LC Packings PepMap C18 column (75 µm×150 mm; particle size 5 µm) for nano-LC separation at a flow rate of 250 nL/min. The eluents used for the LC were (A) 0.1% formic acid (FA) and (B) 95% ACN/0.1% FA and 1%/min gradient was used for the separation. The acquired MS/MS data were searched against the IPI human protein database using Mascot (Matrix Science, Boston, Mass.) database searching engine. Positive protein identification was based on standard Mascot criteria for statistical analysis of LC-MS/MS data.

Immuno-Blotting

Western blotting analysis of alpha-enolase was performed on the same set of saliva samples (10 pSS, 10 controls). Proteins were separated on 12% NUPAGE gels (Invitrogen) at 150 V and then transferred to polyvinylidene difluoride membrane (Bio-Rad) using an Invitrogen blot transfer cell. After saturating with 5% milk in TBST buffer overnight at 4° C., the blots were sequentially incubated with primary goat polyclonal alpha-enolase antibody and horseradish peroxidase-conjugated anti-goat IgG secondary antibody (Santa Cruz Biotechnology, Santa Cruz, Calif.). Finally, the bands were detected by enhanced chemiluminescence (Amersham) and quantified using the software Quantity One (Bio-Rad).

Saliva mRNA Profiling using High-Density Oligonucleotide Microarray

Stimulated PAR or WS saliva from 10 pSS patients and 8 matched controls were preserved in RNAlater reagent (Qiagen, Valencia, Calif.) in a 1:1 ratio and then frozen at −80° C. Total saliva RNA was isolated from 560 ul RNAlater preserved saliva (280 ul PA/WS and 280 ul RNAlater) using Viral RNA mini kit (Qiagen) as described previously (Li et al., *J Dent Res* 2004; 83(3):199-203). Isolated total RNA was treated with two round rDNase I (Ambion, Austin, Tex.) digestion and RNA concentration was measured with Nano-Drop® ND-1000 Spectrophotometer (Wilmington, Del.). The salivary RNA quality was examined by RT-real-time PCR assay for the expression of salivary internal reference gene transcripts S100 calcium-binding protein A8 and annexin A2 (data not shown).

For microarray study, total saliva RNA was subjected to two rounds of T7-based RNA linear amplification (Hu et al., *Int J Oncol* 2004; 25(5):1423-30). One microliter (200 ng/µl) poly (dI-dc) (Amersham, Piscataway, N.J.) was added to 11 µl saliva RNA sample before two rounds of first- and second-strand cDNA synthesis with RiboAmpHS RNA Amplification kit (Arcturus Bioscience, Mountain View, Calif.) according to manufacturer's instructions. After purification, the cDNAs were in vitro transcribed to cRNAs and biotinylated with GeneChip Expression 3'-Amplification Reagents for IVT labeling (Affymetrix, Santa Clara, Calif.). The labeled cRNA was purified with the reagents provided with the Ribo-AmpHS RNA Amplification kit (Arcturus Bioscience). The quality and quantity of amplified cRNA were determined by spectrophotometry with OD260/280 greater than 1.9 for all the samples. Biotinylated cRNA (15 µg each) were subsequently fragmented and quality of the fragmented cRNA was assessed by Aglient 2100 bioanalyzer (Agilent Technologies, Palo Alto, Calif.). The Affymetrix Human Genome U133 plus2 array which contains more than 54,000 probe sets representing more than 47,000 transcripts and variants, including approximately 38,500 well-characterized human genes, was applied to salivary mRNA profiling. Fragmented cRNAs were hybridized overnight to the microarrays. After high-stringency wash to remove the unbound probes, the hybridized chips were stained and scanned according to the AFFYmetrix standard expression protocol. The scanned images were read with the Affymetrix MicroArray robust multi-array average (RMA) software (Irizarry et al., *Nucleic Acids Res* 2003; 31(4):e15).

Statistical Analysis for mRNA Study

The expression microarrays were scanned and the fluorescence intensity was measured by Microarray Suit 5.0 software (Affymetrix). The arrays were then imported into the statistical software R (R Development Core Team. R: A language and environment for statistical computing. R Foundation for Statistical Computing, Vienna, Austria, 2006). After quantile normalization and RMA background correction, the Robust Multi-Array Average (RMA) expression index was computed in R using the Bioconductor (Gentleman et al., *Genome Biol* 2004; 5(10):R80). Because most human RNAs are not present in saliva (Li et al., *J Dent Res* 2004; 83(3): 199-203), using the present/absent call generated by the Affymetrix Microarray Suit 5.0 software, we excluded probe sets that were assigned as "absent" call in most (>75%) of the samples. Principal component analysis (PCA) was performed to assess the information contained in the data to separate pSS and control cases. A two-tailed Student's t test was used for comparison of average gene expression signal intensity between the SS samples (n=10) and controls (n=8). The p-values were adjusted by the Benjamini & Hochberg False Discovery Rate (FDR) (Benjamini, Y., Hochberg, Y., *J Royal Stat Soc* Series B, 1995; 57:289-300). Third, fold ratios between SS and control samples were calculated for the transcripts. For further validation study using real-time quantitative PCR, we applied stringent criteria: alpha level 0.001 for the t-test, which corresponded to 5% FDR based on the data, and fold ratio of 3. For functional analysis using MAPPFinder (Doniger et al., *Genome Biol* 2003; 4(1):R7), we applied alpha level of 0.01, which corresponded to 8% FDR, and fold ratio of 2, to obtain a larger list of genes.

Real-Time Quantitative PCR (RT-qPCR)

The biomarker candidates generated by microarray profiling were validated by RT-qPCR on the same set of samples for microarray analysis. All the primers used for qPCR were designed with the Primer3 and synthesized by Sigma. Total RNA was reverse-transcribed using reverse transcriptase and gene specific primers. One microliter total RNA was used in a 20 µl volume of cDNA synthesis reaction, and the thermal cycling conditions were 25° C. for 10 min, 42° C. for 45 min, and 95° C. for 5 min. Three microliter cDNA was used as template for each 20-µl PCR containing forward primer (200 nM), reverse primer (200 nM), and 10 µl 2×SYBR GREEN PCR master mix (Applied Biosystems). PCRs were carried out on 96-well plate on the Bio-Rad iCycler or IQ5 (95° C. 3 min followed by 50 cycles of 95° C. 30 s, 62° C. 30 s, 72° C. 30 s). All PCRs were performed in duplicates for all candidate mRNAs. After PCR, the specificity of the PCR was confirmed by the melting curve of each gene, and the average threshold cycle was examined. The relative expression of the candidate genes was calculated with 2(delta CT), where Delta CT=CT pSS−CT control, Expression ratio (pSS/control)=2(delta CT) was shown as fold change (Livak et al., *Methods* 2001; 25(4): 402-8).

Gene Ontology Analysis and Analysis of Pathways

Gene ontology analysis using Web-based software GOTree Machine (http://bioinfo.vanderbilt.edu/gotm/) was employed to generate directed cyclic Graph. The PathwayArchitect software, V1.1.0 (Stratagene, La Jolla, Calif.) was used to investigate the functional pathways presented by differentially expressed genes.

Results

Saliva Flow Rate and Total Saliva Protein/mRNA Amount in pSS Patients

Carefully diagnosed and monitored pSS patients were enrolled for this study. All the 10 patients with pSS were positive for anti-SSA/Ro whereas 9 also had anti-SSB/La antibodies. The average IgG level was determined to be 23.4±7.4 (g/l) whereas the IgM rheumatoid factor (IgM-RF) level was 136.3±99.6 (kIU/l). These patients exhibited significantly lower (~50%) saliva flow rates than healthy control subjects. The average stimulated flow rates were 0.13±0.12 (PAR/per gland), 0.32±0.38 (SM/SL), 0.61±0.23 (WS) ml/min for the pSS patients (n=10), and 0.21±0.07 (PAR), 0.78±0.36 (SM/SL) and 1.03±0.31 (whole) ml/min for the control subjects (n=10). Due to the low volume of saliva sample obtained from the pSS patients, the saliva proteins from 10 pSS or 10 control subjects were equally pooled, respectively, for 2-DGE analysis.

On the average, the total protein concentration was determined to be 1.26±0.40 mg/ml (SM/SL, n=8), 0.93±0.38 mg/ml (PAR, n=10) and 0.95±0.52 mg/ml (whole, n=10) for the controls, whereas the average concentration was 1.45±0.49 mg/ml (SM/SL, n=8), 1.40±0.56 mg/ml (PAR, n=10) and 1.38±0.37 mg/ml (whole, n=10) for the pSS patients. Consistently, SS patients' saliva (whole, SM/SL and PAR) contained higher concentration of proteins than the matched healthy subjects. In addition, pSS patients' saliva appeared to contain higher concentration of total RNA than the matched controls. In PAR saliva, the average RNA concentration was determined as 5.8±3.1 µg/ml for pSS patients and 3.6±1.5 µg/ml for matched controls (p=0.05). In WS, the average RNA concentration was 10.9±5.4 µg/ml for pSS patients and 6.6±3.6 µg/ml for matched controls (p=0.057).

Discovery of Candidate Peptide Markers for pSS

FIG. 1A depicts typical MALDI-MS spectra of native peptides in WS samples from a pSS and a matched control subject. Sixteen WS peptides were found at significant differences (p=0.0046–0.0441) between the patient (n=10) and control groups (n=10), including 10 over-expressed ones (m/z, 1107, 1224, 1333, 1380, 1451, 1471, 1680, 1767, 1818, 2039) and 6 under-expressed ones (m/z, 2534, 2915, 2953, 3311, 3930, 4187) in pSS patients. The peptide, m/z of 1451, exhibited the highest up-regulation (25.9 fold) in pSS patients. We also compared the native peptide patterns in PAR and SM/SL saliva between pSS and control subjects (data not shown). WS was found to contain more informative peptides than gland specific (PAR or SM/SL) saliva. On the average, 53 MALDI peaks (n=10) were observed from the WS of pSS patients, whereas only 24 and 26 peaks were detectable from the PAR and SM/SL saliva of pSS patients, respectively.

2-DGE of WS Proteins from pSS and Matched Control Subjects

FIG. 1B presents the 2-DGE patterns of the proteins in pooled WS samples from either 10 pSS or 10 matched control subjects. A number of proteins were found differentially expressed between the pSS and control groups. By performing the PDQuest analysis and normalization of the protein spot signals, the relative levels of these proteins were quantified. The differentially expressed proteins (FIG. 1B, spots 1-42) were excised and subsequently identified using in-gel tryptic digestion and LC-MS/MS. 2-D gel analysis of pooled PAR and SM/SL saliva from pSS and control subjects was also performed (data not shown). WS was again found to be more informative than PAR or SM/SL saliva towards generating candidate protein biomarkers for pSS detection. In total, 325 protein spots were observed from the 2-D gel of WS while 232 and 267 spots were detected from PAR and SM/SL saliva, respectively.

LC-QqTOF MS Identification of Proteins at Altered Expression Levels

Figure 2A:
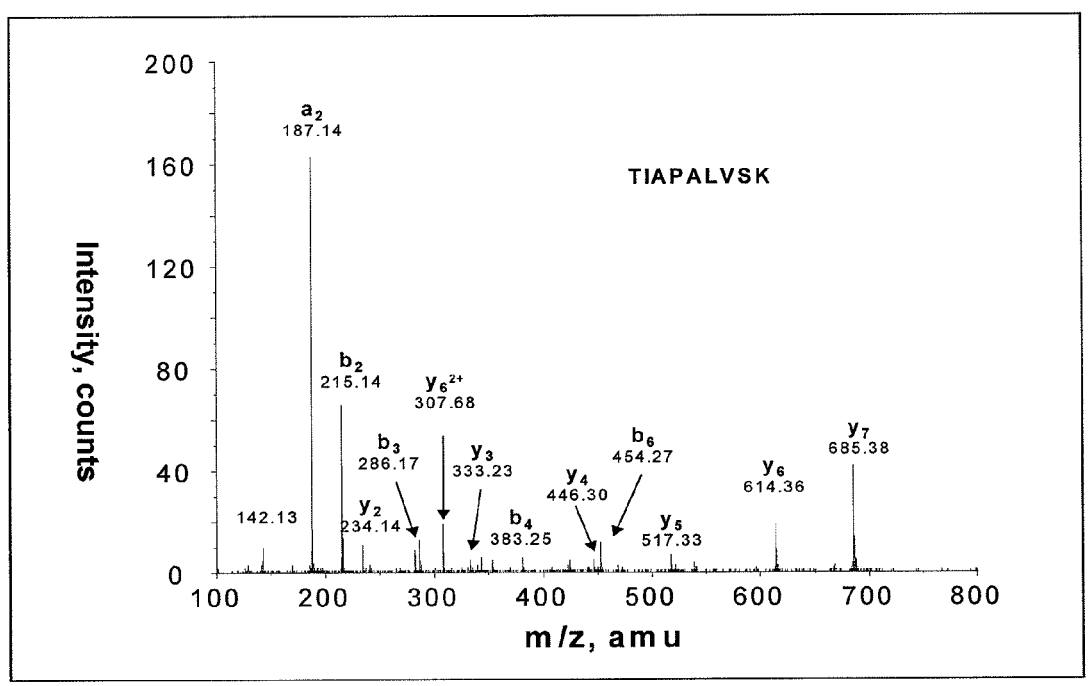
FIG. 2: ESI-MS/MS spectrum of a tryptic peptide, TIAPALVSK (m/z, 450.3), originated from alpha-enolase (A). This protein was found over-expressed in pSS patients' WS by 2-D gel analysis. An equal amount of proteins from each sample was used for immuno-blotting assay of alpha-enolase and actin in the pSS (n=10) and matched control subjects (n=10) (B).
Figure 2B:
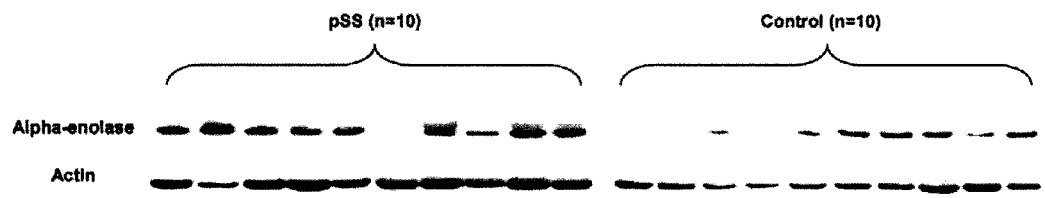

Table 1 lists the differentially expressed WS proteins identified by LC-QqTOF MS and Mascot database searching as well as their theoretical molecular weight (Mr), isoelectric point (pI), IPI accession number, matched peptide number and ratios of expression levels between pSS and matched control groups. FIG. 2A depicts the tandem MS spectrum of a double-charged, tryptic peptide (m/z, 450.3). The precursor ion was well fragmented to yield sufficient structural information for confident identification of the peptide sequence, TIAPALVSK, originated from alpha-enolase. Mascot database searching indicated that 12 peptides were matched to this protein, resulting in a sequence-coverage of 31%. Validation of alpha-enolase was also performed by western blotting on the same set of samples used for the 2DGE study (FIG. 2B). An equal amount of total proteins from each sample was used for immuno-blotting assay of alpha-enolase and actin. Both alpha-enolase and actin were found up-regulated in the WS of pSS patients, which is consistent with 2-D gel results (Table 1). The p value was determined as 0.006 for alpha-enolase without actin normalization, whereas if actin was used for normalization, a p value of 0.037 was obtained for alpha-enolase between the pSS and control groups.

Discovery of Saliva Candidate Genomic Markers for pSS

For all the arrays, the average percentage (P %) of present genes was 13.2±2.9. This is similar to our previously report (Li et al., *J Dent Res* 2004; 83(3):199-203) indicating the consistency of the techniques in sample preparation. Microarray profiling indicated that WS contains over 10 times more informative mRNAs than PAR saliva. In total, 328 mRNAs were found above 2-fold change in WS, while only 21 mRNAs were found above 2-fold change in PAR saliva. Therefore, we focused on discovery and validation of WS candidate mRNA biomarkers using microarray and RT-qPCR strategies.

Figure 3:
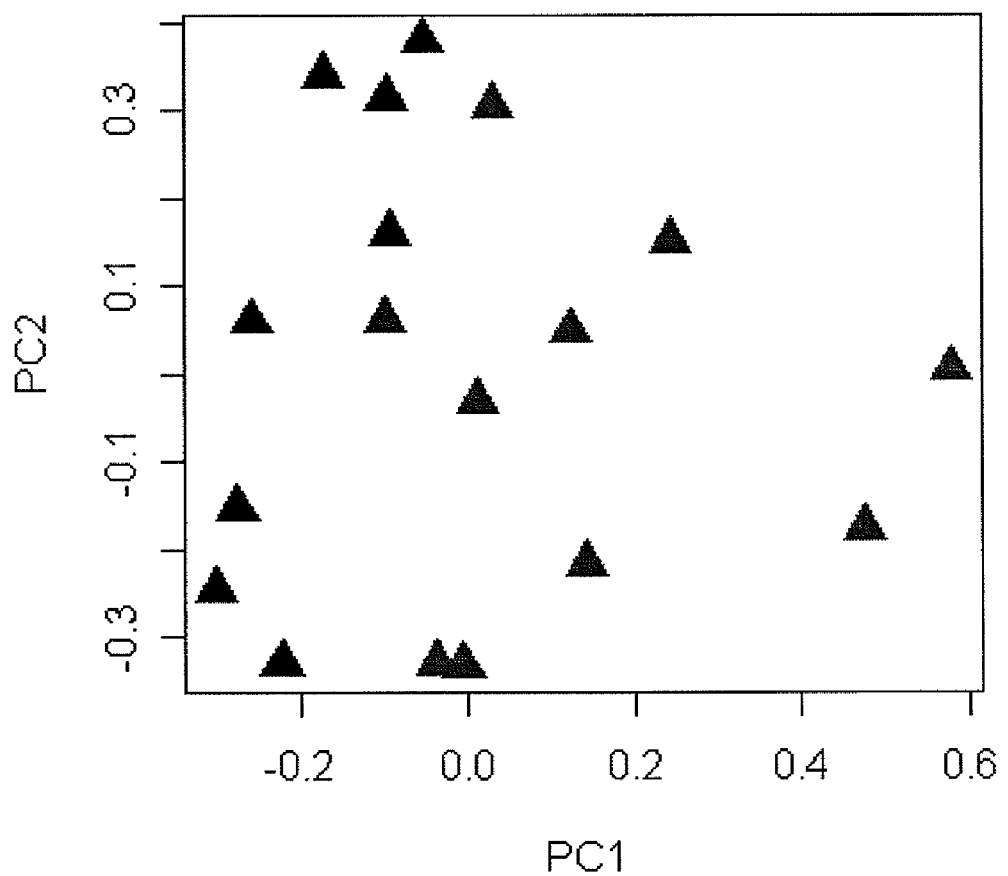
FIG. 3: Principal component analysis suggests that the obtained gene expression data can segregate the control and pSS subjects. The projection onto the first two PCs represents control (blue) and pSS (red).

Gene expression profiling of individual WS samples from 10 pSS and 8 controls were compared. After filtering the transcripts by the criteria of being "present" in more than 25% of the samples, 6413 transcripts were retained for further analysis. The number is consistent with our previous results that only a small fraction of RNAs are present in saliva (Li et al., J Dent Res 2004; 83(3):199-203). PCA analysis indicated that the information contained in the data could well segregate control and pSS subjects (FIG. 3). We then performed statistical testing and fold change analysis to identify differentially expressed genes. Only a few mRNAs were found at significantly lower level in pSS patients comparing to the control subjects when using a threshold of >2-fold change and $p<0.01$ (FDR=0.08). Yet by the same criteria, 162 genes showed significant up-regulation in pSS samples. Gene ontology analysis was used to classify 162 differentially expressed genes into their functional relationships on the basis of biology processes. Three clusters were formed: the first cluster leading to JAK-STAT cascade, the second associated with the induction of apoptosis, and the third resulted in immune responses: antimicrobial humoral response, antigen processing and presentation of endogenous peptide antigen via MHC class I. Pathway analysis indicated that 37 genes were involved in the interferon-α pathway and most of them have been reported to be IFN-alpha or IFN-beta inducible (Der et al., *Proc Natl Acad Sci USA* 1998; 95(26):15623-8; Sanda et al., *J Interferon Cytokine Res* 2006; 26(7):462-72). These results suggest the involvement of activation of IFN pathways in the pathogenesis of pSS and that the related information is reflected in the saliva. To facilitate biomarker discovery, we narrowed down the biomarker candidates by using more stringent criteria of $p<0.001$ (FDR=0.05) and 3 fold change, and 27 genes were found all highly over-expressed in pSS samples. These genes are informative sufficiently for segregating the pSS from control subjects (FIG. 4).

Among the top 27 genes, 13 genes were validated by RT-qPCR. Eleven genes were found significantly up-regulated in pSS patients (fold change>10), including interferon-α-inducible protein G1P2 with ~500 fold change in pSS patients. Table 2 shows the average Ct values of these genes in pSS and control subjects, as well as qPCR fold change in comparison with that of microarray profiling.

Discussion

Although saliva has been extensively explored as a source for diagnosis of pSS, most of the previously published studies mainly looked into individual salivary components. High throughput profiling techniques, such as proteomics and expression microarray, enable us to explore saliva proteins and mRNAs in a global fashion, and therefore may provide new and deeper insights to the discovery of saliva biomarkers for pSS. Recently, surface-enhanced laser desorption/ionization time-of-flight (SELDI-TOF) MS and differential gel electrophoresis have been used to discover very promising candidate biomarkers in tear fluid and PAR saliva for SS (Tomosugi et al., *J. Proteome Res* 2005; 4(3):820-5; Ryu et al., *Rheumatology* (Oxford) 2006; 45(9):1077-86). It was found that the PAR saliva proteomic profile of SS is a mixture of increased inflammatory proteins and decreased acinar proteins as compared with non-SS controls (Ryu et al., *Rheumatology* (Oxford) 2006; 45(9):1077-86).

In order to determine which oral fluid compartment is more informative towards biomarker discovery for pSS detection, we utilized both proteomic or microarray approaches to profile peptides, proteins or mRNAs in whole, PAR and SM/SL saliva from the same individual. WS as a fluid includes secretions from three major salivary glands, numerous minor salivary glands, gingival fluid, as well as cells debris. There has been concern about the high background in WS for a specific disease, while PAR saliva, if collected carefully, may be more gland-specific. Yet the literature has no report of the advantages of gland specific saliva versus WS in terms of diagnostic potential for pSS. Our study allows us to conclude that WS is more informative than glandular saliva towards generating biomarkers for pSS detection. Microarray profiling indicated that WS of pSS patients contains 328 mRNAs with 2-fold expression change, whereas the PAR saliva of pSS patients contains only 21 mRNAs above 2-fold change. Similarly, MALDI-TOF MS and 2-DGE analyses suggested that WS from pSS patients has more informative proteomic components than PAR or SM/SL saliva. Since the saliva flow rate varies from individual to individual, the peptide or protein compositions among different individuals could be affected by the very low flow rate of PAR and SM/SL saliva. Considering the low flow rate of glandular saliva as well as the additional skill set and clinical time necessary to collect gland specific saliva, WS may be a more appropriate clinical diagnostic fluid for pSS biomarker discovery and detection.

The panel of candidate peptide/protein markers for pSS is completely distinct from the one we observed for oral cancer (Hu et al., Discovery of oral fluid biomarkers for human oral cancer using mass spectrometry, Cancer Genomics Proteomics 2006; in press). This suggests that the panels of discriminatory salivary proteomic components are likely to be different for different diseases. The majority of under-expressed proteins found in pSS patients' WS are secretory proteins including three glycoforms of carbonic anhydrase VI (FIG. 1B, spots 1-3), cystatins, lysozyme C, polymeric-immunoglobulin receptor (pIgR), calgranulin A, prolactin inducible protein (PIP) and Von Ebner's gland protein (VEGP). This suggests that the level of secretory proteins in WS of pSS patients may be directly affected by injury to salivary glandular cells. Several of these down-regulated proteins in WS of pSS patients, including pIgR, lysozyme C and cystatin C, were found up-regulated in the PAR saliva of pSS patients in a previous publication. This may be factual as evidenced by our comparative analysis of PAR saliva proteins between pSS and control subjects (data not shown). For instance, in our 2-DGE study, pIgR was also found up-regulated in the pooled PAR saliva of pSS patients as compared to the matched subjects (data not shown). A future study of the PAR saliva protein profile versus the WS protein profile from the same pSS patients would be of interest to the pSS research community.

Two glycolysis enzymes, fructose-bisphosphate aldolase (FBPA) and alpha-enolase, were found at elevated levels in the WS of pSS patients. FBPA plays a central role in glucose metabolism, catalyzing either net cleavage or synthesis during glycolysis or gluconeogenesis. Alpha-enolase is a multifunctional glycosis enzyme involved in various processes such as growth control, hypoxia tolerance and allergic responses. Previously, alpha-enolase was identified as an autoantigen in Hashimoto's encephalopathy, which is an autoimmune disease associated with Hashimoto's thyroiditis (Ochi et al., *FEBS Lett* 2002; 528(1-3):197-202). Alpha-enolase was also found as an autoantigen in lymphocytic hypophysitis (LHP), and serum autoantibodies directed against alpha-enolase were detected in LHP patients as well as other autoimmune diseases. Excessive production of autoantibodies, which are generated as a consequence of uptake of enolase by antigen-presenting cells and subsequent B cell activation, can potentially initiate tissue injury as a result of immune complex deposition (O'Dwyer et al., *J Clin Endocrinol Metab* 2002; 87(2):752-7; Pratesi et al., *J Rheumatol* 2000; 27(1):109-15). Over-expressed proteins in pSS patients' WS also included psoriasin, fatty acid-binding protein (FABP), CA I & II, salivary amylase fragments, caspase 14, B2M, hemoglobin (beta and alpha-1 global chains) and immunoglobulins. The elevated level of caspase 14 protein and caspase 1 and 4 RNA in pSS patients also suggested an interesting role of apoptosis in pSS pathogenesis process.

Our study clearly demonstrates that pSS-related gene expression signatures are present in saliva and they are able to differentiate pSS from control subjects. To our best knowledge, this is the first study on discovery of candidate saliva mRNA markers for pSS detection. One hundred and sixty-two differentially expressed genes show up in saliva of pSS as compared to 35 and 424 found in microarray profiling of minor salivary gland biopsies (Gottenberg et al., *Proc Natl Acad Sci USA* 2006; 103(8):2770-5; Hjelmervik et al., *Arthritis Rheum* 2005; 52(5):1534-44), respectively. One of the important findings for this study is that the 37 up-regulated genes in pSS patients' saliva were involved in the IFN pathway. This further confirmed the findings from previous tissue-based studies and demonstrated that the IFN-inducible gene signature associated with pSS can be reflected in pSS patients' saliva (Gottenberg et al., *Proc Natl Acad Sci USA* 2006; 103(8):2770-5; Hjelmervik et al., *Arthritis Rheum* 2005; 52(5):1534-44; Bave et al., *Arthritis Rheum.* 2005; 52(4):1185-95; Baechler et al., *Immunol Rev* 2006; 210:120-37). Beyond the IFN-inducible genes, the class I major histocompatibility complex is another major group of up-regulated genes found common to salivary gland and saliva from patients with pSS (Gottenberg et al., *Proc Natl Acad Sci USA* 2006; 103(8):2770-5; Hjelmervik et al., *Arthritis Rheum* 2005; 52(5):1534-44). In addition, there are other genes reported to be particular interest in the pathogenesis of pSS (Hjelmervik et al., *Arthritis Rheum* 2005; 52(5):1534-44) found over-expressed in pSS saliva. For examples, proteasome subunit β, type 9 (PSMB9), guanylate binding protein 2 (GBP2), interferon-induced, hepatitis C virus-associated (IFI44), as well as interferon-α-inducible protein, 15 kd (GIP2) and beta 2-microglobulin (B2M) are all among the common differential expressed genes. These common genes found in saliva and minor salivary gland tissue from patients with pSS are markers (e.g., IFN-inducible genes; class I major histocompatibility complex genes, genes reported to be particular interest in the pathogenesis of pSS; proteasome subunit β, type 9 (PSMB9), guanylate binding protein 2 (GBP2), interferon-induced, hepatitis C virus-associated (IFI44), as well as interferon-α-inducible protein, 15 kd (GIP2) and beta 2-microglobulin (B2M)) according to the invention and support our hypothesis that saliva harbors the biomarkers for pSS.

The mechanism of interferon pathway activation in the pathogenesis of pSS may be more complicated. Activation of IFN pathways (both type I and type II) suggests the involvement of virus infection in the pathogenesis of pSS. Immune complexes consisting of autoantibodies and DNA- or RNA-containing auto-antigens derived from apoptotic or necrotic cells are also able to induce the production of type I IFN. However, IFN itself is not in the gene list found over-expressed in pSS patients' saliva. On the other hand, low dose of IFN-alpha has been reported to be effective in the treatment of some patients with pSS (Shiozawa et al., *J. Interferon Cytokine Res* 1998; 18(4):255-62; Ferraccioli et al., *Clin Exp Rheumatol* 1996; 14(4):367-71). For example, a single-blinded controlled trial has shown that IFN-alpha therapy significantly improves SS salivary gland dysfunction. Serial labial salivary gland biopsies of 9 IFN-alpha responding patients showed that lymphocytic infiltration was significantly decreased (p<0.02) and the proportion of intact salivary gland tissue was significantly increased (p=0.004) after IFN-alpha treatment. Type I interferon pathway dysregulation, however, has been reported also in distinct diseases, such as systemic lupus erythematosus, dermatomyositis, and psoriasis as well as SS (Gottenberg et al., *Proc Natl Acad Sci USA* 2006; 103(8):2770-5), indicating that the consequence of activation along the same pathway is, likely, tissue type dependent, and from a therapeutical point of view, local immune modulation e.g. directly infusion the therapeutic reagent, such as gene therapeutics into salivary glands, may be more efficient than systemic interference. The initial viral infection-induced type I IFN production in salivary glands and prolonged activation triggered by autoantibodies form nucleic-acid-containing immune complexes has been proposed as the mechanism in the pSS (Nordmark et al., *Nat Clin Pract Rheumatol* 2006, 2(5):262-9). More importantly, this IFN-pathway activation may provide potential therapeutic targets for pSS, and saliva may be used to monitor the response to the IFN-related target modulation.

One of the up-regulated genes in pSS patients' saliva, also IFN regulated, is salivary B2M. Significantly elevated levels of B2M have been previously detected in saliva from patients with pSS (Swaak et al., *Clin Rheumatol* 1988; 7(1):28-34). Salivary (but not serum) concentration of B2M was highly related to the salivary gland biopsy focus score. The value of salivary B2M protein as a biomarker for pSS has been evaluated and determination of beta B2M in the saliva used as a noninvasive measurement for the confirmation of the diagnosis of SS has been suggested (Maddali Bongi et al., *Clin Rheumatol* 1995; 14(2):151-6). Interestingly but not surprisingly, we found that both B2M mRNA and protein levels are concordantly over-expressed in pSS patients' saliva.

From the top 27 over-expressed mRNAs in pSS patients' WS as revealed by microarray profiling, 11 genes were validated whereas the expression of the other 16 genes in WS was too low for qPCR. The most over-expressed mRNA was found to be G1P2, which has a function in cell signaling and has been reported to be up-regulated at mRNA level in pSS minor salivary glands (Hjelmervik et al., *Arthritis Rheum* 2005; 52(5):1534-44). Our data suggested that most of the microarray results were validatable by qPCR. There is discrepancy regarding the fold changes between qPCR validation and microarray assay. Many factors may contribute to this discrepancy including procedures unique to microarray, such as non-specific and/or cross hybridizations of labeled targets to array probes, as well as to RT and Real-time PCR such as amplification biases (Chuaqui et al., *Nat Genet* 2002; 32 Suppl:509-14). Also the increase distance between the location of the PCR primers and microarray probes on a given gene was found to decrease the correlation between the two methods (Etienne et al., *Biotechniques* 2004; 36(4):618-26). In this particular study, the amplified RNA used for microarray assay and non-amplified RNA used in RT and real-time PCR may potentially introduce variances on the fold changes between these two methods. For those genes whose expression is too low for qPCR, it is still possible to detect them by increasing the template amount, e.g. more RNA to start, when increased amount of saliva can be obtained from pSS patients. Nevertheless, these 11 highly expressed genes, once further validated on a new and independent patient cohort, may be used in clinical detection of pSS.

There was little correlation between the discovered protein and mRNA markers. This has been observed for biological systems when efforts were made to correlate the gene expression at both protein and mRNA levels (Gygi et al., *Mol Cell Biol* 1999; 19(3):1720-30; Baliga et al., *Proc Natl Acad Sci USA* 2002; 99(23):14913-8). In a previous study on correlation analysis of human saliva proteome and transcriptome, we demonstrated that complementary validation (e.g., western blotting for protein or RT-PCR for mRNA) is required in the conduct of RNA-protein correlation study on individual genes after initial MS and expression microarray profiling (Hu et al., *J Dent Res* 2006, 85(12):1129-33). We may foresee higher correlation of the discovered protein and mRNA candidate markers if mutual validation is performed. Nevertheless, the discrepancy may suggest that the combination of both mRNA and protein markers is important for improving pSS detection. As a result of this study, a number of promising saliva protein and mRNA candidates that are characteristic of pSS have been identified. Many of these candidate biomarkers have not been associated previously with SS, and as a combination, they may be eventually developed for the clinical diagnosis of pSS. The discovered panel of genes may also be mapped on biochemical pathways to unveil the possible mechanisms underlying this disease. Tracing the pathways of those genes (e.g., caspases in apoptosis) in pSS progression may lead to better treatment and prevention of this specific autoimmune disease.

In summary, our preliminary study has demonstrated that WS is an informative body fluid for the detection of pSS, in a totally non-invasive fashion, although the findings obtained in this study certainly need to be further validated. Ideal biomarkers need to be very specific for pSS and should discriminate pSS from other autoimmune diseases with a similar immuno-pathological background. Future study will be to include new pSS patients as well as patients with other autoimmune diseases as control groups, aiming to validate those candidate genes either using RT-qPCR for mRNA or immunoassays for proteins. Absolute quantification will provide a cutoff for each biomarker selected and a multi-marker prediction model by combining mRNA and protein markers will be eventually built and tested for the clinical diagnosis of pSS.

TABLE 1

| Spot No. | Accession | Protein name | Mascot score | Peptide matched | pI$^a$ | Mr$^a$ | Ratio (pSS/ctrl) |
|---|---|---|---|---|---|---|---|
| 1 | IPI00295105 | Carbonic anhydrase VI | 163 | 4 | 6.65 | 35343 | 0.22 |
| 2 | IPI00295105 | Carbonic anhydrase VI | 114 | 5 | 6.65 | 35343 | 0.35 |
| 3 | IPI00295105 | Carbonic anhydrase VI | 78 | 2 | 6.65 | 35343 | 0.29 |
| 4 | IPI00004573 | Polymeric-immunoglobulin receptor | 235 | 5 | 5.58 | 83262 | 0.48 |
| 5 | IPI00004573 | Polymeric-immunoglobulin receptor | 293 | 7 | 5.58 | 83262 | 0.39 |
| 6 | IPI00004573 | Polymeric-immunoglobulin receptor | 182 | 4 | 5.58 | 83262 | 0.56 |
| 7 | IPI00019038 | Lysozyme C | 103 | 2 | 9.38 | 16526 | 0.21 |
| 8 | IPI00022974 | Prolactin-inducible protein | 147 | 3 | 8.26 | 16562 | 0.52 |
| 9 | IPI00009650 | Von Ebner's gland protein | 239 | 4 | 5.39 | 19238 | 0.32 |
| 10 | IPI00032293 | Cystatin C | 153 | 3 | 9.0 | 15789 | 0.43 |
| 11 | IPI00013382 | Cystatin SN | 152 | 3 | 6.82 | 16361 | 0.46 |
| 12 | IPI00013382 | Cystatin SN | 130 | 3 | 6.82 | 16361 | 0.61 |
| 13 | IPI00002851 | Cystatin D | 50 | 1 | 6.70 | 16070 | 0.56 |
| 14 | IPI00032294 | Cystatin S | 166 | 3 | 4.95 | 16214 | 0.65 |
|  | IPI00013382 | Cystatin SA | 208 | 4 | 4.85 | 16445 |  |
| 15 | IPI00007047 | Calgranulin A | 104 | 2 | 6.51 | 10828 | 0.53 |
| 16 | IPI00007047 | Calgranulin A | 79 | 2 | 6.51 | 10828 | Absent in pSS |
| 17 | IPI00027462 | Calgranulin B | 126 | 4 | 5.71 | 13234 | 1.05 |
| 18 | IPI00219806 | Psoriasin | 133 | 4 | 6.28 | 11464 | 1.44 |
| 19 | IPI00410714 | Hemoglobin alpha-1 globin chain | 157 | 5 | 7.96 | 15292 | Absent in control |
| 20 | IPI00218816 | Hemoglobin beta chain | 48 | 1 | 6.75 | 15988 | 2.73 |
| 21 | IPI00218816 | Hemoglobin beta chain | 51 | 1 | 6.75 | 15988 | 7.58 |
| 22 | IPI00007797 | Fatty acid-binding protein, epidermal | 211 | 6 | 6.60 | 15155 | 3.21 |
| 23 | IPI00472762 | IGHG1 protein | 333 | 14 | 8.33 | 50822 | 22.64 |
|  | IPI00472610 | Hypothetical protein | 363 | 14 | 7.50 | 52633 |  |
|  | IPI00430840 | Ig gamma-1 chain C region | 333 | 14 | 7.48 | 54866 |  |
| 24 | IPI00472610 | IGHM protein | 260 | 11 | 7.50 | 53270 | Absent in control |
|  | IPI00550718 | Ig gamma-1 chain C region | 257 | 11 | 8.46 | 53331 |  |
| 25 | IPI00465248 | Alpha-enolase | 409 | 12 | 6.99 | 47139 | 4.37 |
| 26 | IPI00300786 | Salivary alpha-amylase, fragment | 241 | 5 | 5.73 | 57731 | 3.41 |
| 27 | IPI00300786 | Salivary alpha-amylase, fragment | 230 | 4 | 5.73 | 57731 | 2.19 |

TABLE 1-continued

| Spot No. | Accession | Protein name | Mascot score | Peptide matched | pI$^a$ | Mr$^a$ | Ratio (pSS/ctrl) |
|---|---|---|---|---|---|---|---|
| 28 | IPI00300786 | Salivary alpha-amylase, fragment | 375 | 7 | 5.73 | 57731 | 31.53 |
| 29 | IPI00300786 | Salivary alpha-amylase, fragment | 260 | 5 | 5.73 | 57731 | 2.57 |
| 30 | IPI00300786 | Salivary alpha-amylase, fragment | 171 | 5 | 5.73 | 57731 | 2.50 |
| 31 | IPI00300786 | Salivary alpha-amylase, fragment | 194 | 4 | 5.73 | 57731 | 11.92 |
| 32 | IPI00300786 | Salivary alpha-amylase, fragment | 149 | 4 | 5.73 | 57731 | 1.57 |
| 33 | IPI00300786 | Salivary alpha-amylase, fragment | 148 | 4 | 5.73 | 57731 | 4.03 |
| 34 | IPI00549682 | Fructose-bisphosphate aldolase A | 218 | 4 | 8.75 | 52306 | 2.59 |
| 35 | IP100332161 | Ig gamma-1 chain C region | 138 | 5 | 8.46 | 36083 | 2.54 |
| 36 | IPI00215983 | Carbonic anhydrase I | 119 | 4 | 6.59 | 28852 | 7.4 |
| 37 | IPI00218414 | Carbonic anhydrase II | 98 | 2 | 8.67 | 31337 | 2.11 |
| 38 | IPI00013885 | Caspase-14 & Cathepsin D | 172 | 5 | 5.44 | 27662 | 3.32 |
| 39 | IPI00419424 | Ig kappa chain C region | 263 | 7 | 5.82 | 27313 | 1.79 |
| 40 | IPI00004656 | Beta-2-microglobulin | 62 | 2 | 6.06 | 13706 | 2.21 |
| 41 | IP100021439 | Actin | 461 | 11 | 5.29 | 41710 | 3.18 |
| 42 | IPI00022434 | Serum albumin, fragment | 492 | 10 | 5.41 | 69321 | Absent in control |

TABLE 2

| Gene symbol | Average Ct Control | Average Ct pSS | Δ Ct (Control/pSS) | qPCR fold-change ($2^Δ$) | P value (t-test) | Microarray fold change* |
|---|---|---|---|---|---|---|
| GIP2 | 44.5 ± 1.9 | 35.5 ± 2.1 | 9.0 | 495.5 | <0.001 | 15.76 |
| B2M | 45.0 ± 2.1 | 38.8 ± 3.4 | 6.2 | 72.1 | <0.001 | 8.67 |
| IFIT2 | 41.1 ± 2.0 | 35.9 ± 2.6 | 5.1 | 35.5 | <0.001 | 12.19 |
| BTG2 | 38.5 ± 5.3 | 33.5 ± 2.0 | 5.0 | 32.4 | 0.01 | 3.22 |
| IFIT3 | 43.8 ± 0.5 | 39.1 ± 2.4 | 4.7 | 25.3 | <0.001 | 122.82 |
| MNDA | 37.3 ± 1.2 | 33.7 ± 2.1 | 3.7 | 12.7 | <0.001 | 8.67 |
| FCGR3B | 40.6 ± 1.5 | 36.9 ± 2.2 | 3.6 | 12.5 | <0.001 | 25.32 |
| TXNIP | 39.2 ± 2.1 | 35.6 ± 3.2 | 3.6 | 11.7 | 0.01 | 3.42 |
| IL18 | 45.3 ± 2.1 | 41.8 ± 2.5 | 3.5 | 11.5 | 0.01 | 6.12 |
| HLAB | 36.4 ± 2.7 | 32.9 ± 2.0 | 3.5 | 11.2 | 0.01 | 4.34 |
| EGR1 | 37.4 ± 2.4 | 33.9 ± 2.0 | 3.4 | 10.3 | 0.01 | 7.20 |
| COP1 | 40.5 ± 1.5 | 38.7 ± 3.3 | 1.8 | 3.4 | 0.18 | 7.62 |
| TNSF | 39.6 ± 0.4 | 38.9 ± 2.9 | 0.7 | 1.6 | 0.95 | 8.03 |

TABLE 3

| Database ID | Ultimate ORF ID | Protein Description |
|---|---|---|
| BC014051.1 | IOH14549 | small inducible cytokine subfamily E, member 1 (endothelial monocyte-activating) (SCYE1) |
| NM_022101.1 | IOH27781 | chromosome X open reading frame 56 (CXorf56) |
| Ro-52 | | Ro-52/SSA - known Autoantigen |
| NM_015993.1 | IOH5384 | plasma membrane proteolipid (plasmolipin) (PLLP) |
| BC010629.1 | IOH9802 | outer dense fiber of sperm tails 2 (ODF2) |
| BC034554.1 | IOH25751 | serpin peptidase inhibitor, clade A (alpha-1 antiproteinase, antitrypsin), member 3 (SERPINA3) |
| La | | La/SS-B (La) - known Autoantigen |
| PV3652 | | TAO kinase 3 (TAOK3) |
| NM_024946.1 | IOH10395 | NEFA-interacting nuclear protein NIP30 (NIP30) |
| XM_375456.2 | IOH43380 | hypothetical protein DKFZp761G2113 |
| BC053667.1 | IOH29009 | lectin, galactoside-binding, soluble, 3 (galectin 3) |
| P2996 | | protein kinase C, theta (PRKCQ) |
| BC069328.1 | IOH40255 | Bcl2 modifying factor (BMF) |
| TRANSGLUTAMINASE | TRANSGLUTAMINASE - known Autoantigen | |

TABLE 3-continued

| Database ID | Ultimate ORF ID | Protein Description |
|---|---|---|
| NM_002307.1 | IOH40009 | lectin, galactoside-binding, soluble, 7 (galectin 7) (LGALS7) |
| PV3831 | | ribosomal protein S6 kinase, 70 kDa, polypeptide 2 (RPS6KB2) |
| PV3370 | | megakaryocyte-associated tyrosine kinase (MATK) |
| CARDIOLIPIN | CARDIOLIPIN - known Autoantigen | |
| histone | | UNFRAC. WHOLE HISTONE - known Autoantigen |
| BC028366.1 | IOH22335 | testis specific, 10 (TSGA10) |
| NM_004527.2 | IOH40231 | mesenchyme homeo box 1 (MEOX1) |
| NM_018664.1 | IOH44746 | Jun dimerization protein p21SNFT (SNFT) |
| AB065630.1 | IOH28294 | olfactory receptor, family 6, subfamily N, member 2 (OR6N2) |
| BC032852.2 | IOH27153 | melanoma antigen family B, 4 (MAGEB4) |

TABLE 4

| Public ID | Gene Title | t-test p-value | fold change |
|---|---|---|---|
| AI075407 | Interferon-induced protein with tetratricopeptide repeats 3 | 4.65E−08 | 122.8183 |
| J04162 | Fc fragment of IgG, low affinity IIIb, receptor (CD16b) | 8.88E−05 | 25.31635 |
| NM_005101 | Interferon, alpha-induced protein (clone IFI-15K) | 1.04E−06 | 15.75892 |
| AA131041 | Interferon-induced protein with tetratricopeptide repeats 2 | 6.23E−06 | 12.18509 |
| NM_001548 | Interferon-induced protein with tetratricopeptide repeats 1 | 7.60E−06 | 10.90116 |
| AW188940 | Beta-2-microglobulin | 0.000213 | 8.674713 |
| NM_002432 | Myeloid cell nuclear differentiation antigen | 2.53E−05 | 8.668901 |
| AF134715 | Tumor necrosis factor (ligand) superfamily, member 13b | 0.000197 | 8.034189 |
| AW071793 | MAX dimerization protein 1 | 6.26E−05 | 7.750381 |
| NM_052889 | CARD only protein | 1.27E−06 | 7.619491 |
| NM_001964 | Early growth response 1 | 0.000821 | 7.196205 |
| NM_003853 | Interleukin 18 receptor accessory protein | 0.000303 | 6.117933 |
| U73191 | Potassium inwardly-rectifying channel, subfamily J, member 15 | 0.000127 | 5.828243 |
| AI742057 | Hypothetical protein LOC129607 | 1.07E−05 | 5.614856 |
| NM_000698 | Arachidonate 5-lipoxygenase | 0.000303 | 5.528699 |
| AW189843 | Radical S-adenosyl methionine domain containing 2 | 3.15E−05 | 5.373925 |
| AI421071 | Chemokine (C-C motif) receptor 1 | 0.000671 | 5.154625 |
| AB055977 | Brain protein 13 | 0.00017 | 4.959552 |
| L42024 | Major histocompatibility complex, class I, B | 0.000383 | 4.335634 |
| NM_002800 | Proteasome (prosome, macropain) subunit, beta type, 9 | 0.000155 | 4.266731 |
| NM_021122 | Acyl-CoA synthetase long-chain family member 1 | 6.00E−05 | 3.997893 |
| NM_006763 | BTG family, member 2 | 0.00055 | 3.900431 |
| AA005023 | Nucleotide-binding oligomerization domains 27 | 0.000832 | 3.778998 |
| BC000715 | C-type lectin domain family 4, member E | 0.000314 | 3.576164 |
| NM_006472 | Thioredoxin interacting protein | 0.000581 | 3.420311 |
| NM_004120 | Guanylate binding protein 2, interferon-inducible | 0.000843 | 3.219133 |
| NM_016323 | Hect domain and RLD 5 | 0.000113 | 3.071258 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for diagnosing Sjögren's Syndrome in a subject, the method comprising the steps of:
  (a) analyzing a saliva sample from the subject with an assay that specifically detects the level of a marker selected from Table 1, Table 4, or FIG. 4; and
  (b) determining whether the marker level is increased or decreased from a standard control, wherein the increase for IGHG1 protein hypothetical protein Ig gamma-1 chain C region (protein #23, Table 1), Ig gamma-1 chain C region (protein 35, Table 1) and Ig kappa chain C region (protein 39, Table 1) is 1.79 or more relative to a control as measured by LC QpTOF MS; and thereby providing a diagnosis for Sjögren's Syndrome.

2. The method of claim 1, wherein the assay detects protein and is ELISA, Western blotting, flow cytometry, immunofluorescence, immunohistochemistry, or mass spectroscopy.

3. The method of claim 1, wherein the assay comprises a reagent that binds to a protein.

4. The method of claim 3, wherein the reagent is an antibody.

5. The method of claim 4, wherein the reagent is a monoclonal antibody.

6. The method of claim 3, wherein the assay is ELISA, Western blotting, flow cytometry, immunofluorescence, immunohistochemistry, mass spectroscopy.

7. The method of claim 1, wherein the marker is a protein selected from proteins 1-16 of Table 1 and a decreased marker level indicates Sjögren's Syndrome.

8. The method of claim 1, wherein the marker is a protein selected from proteins 18-42 of Table 1 and an increased marker level indicates Sjögren's Syndrome.

9. A method of providing a prognosis for Sjögren's Syndrome in a subject, the method comprising the steps of:
  (a) analyzing a saliva sample from the subject with an assay that specifically detects the level of a marker selected from Table 1 or FIG. 4; and
  (b) determining whether the marker level is increased or decreased from a standard control, wherein the increase for IGHG1 protein hypothetical protein Ig gamma-1 chain C region (protein #23, Table 1), Ig gamma-1 chain C region (protein #35, Table 1) and Ig kappa chain C region (protein #39, Table 1) is 1.79 or more relative to a control as measured by LC QpTOF MS; and thereby providing a prognosis for Sjögren's Syndrome.

10. A method for diagnosing Sjögren's Syndrome in a subject, the method comprising the steps of
  (a) analyzing a saliva sample from the subject with an assay that specifically detects the level of a Cathespin D and
  (b) determining whether the level of Cathespin D is increased from a standard control; and thereby providing a diagnosis for Sjögren's Syndrome.

11. The method of claim 10, wherein the assay is ELISA, Western blotting, flow cytometry, immunofluorescence, immunohistochemistry, or mass spectroscopy.

12. The method of claim 11, wherein the assay is ELISA.

* * * * *